United States Patent [19]

Luedders

[11] 4,299,826
[45] Nov. 10, 1981

[54] ANTI-ACNE COMPOSITION

[75] Inventor: Wilmer L. Luedders, Cincinnati, Ohio

[73] Assignee: The Procter & Gamble Company, Cincinnati, Ohio

[21] Appl. No.: 84,252

[22] Filed: Oct. 12, 1979

[51] Int. Cl.³ ............................................. A61K 31/71
[52] U.S. Cl. .................................... 424/181; 424/365
[58] Field of Search ............................... 424/181, 365

[56] References Cited

U.S. PATENT DOCUMENTS

| | | | |
|---|---|---|---|
| 3,952,099 | 4/1976 | Smith | 424/227 |
| 3,969,516 | 7/1976 | Stoughton | 424/181 |
| 4,132,781 | 1/1979 | Stoughton | 424/181 |

FOREIGN PATENT DOCUMENTS 2383667 10/1978 France .

Primary Examiner—Leonard Schenkman
Attorney, Agent, or Firm—R. C. Witte; J. D. Schaeffer; M. J. Roth

[57] ABSTRACT

Compositions for topical application of erythromycin and derivatives of erythromycin, comprising an erythromycin compound and a member selected from the group consisting of lauryl alcohol, diisopropyl sebacate, dibutyl sebacate, dioctyl adipate, propylene glycol dipelargonate, ethyl laurate, butyl laurate, ethyl myristate, butyl myristate, isopropyl palmitate, oleyl alcohol, diethyl sebacate, dioctyl sebacate, dioctyl azelate, hexyl laurate, ethyl caprate, butyl stearate, isopropyl isostearate, 2-ethyl-hexyl pelargonate, butyl benzoate, benzyl benzoate, benzyl salicylate, and dibutyl phthalate, and mixtures thereof, are especially useful as a treatment for acne.

14 Claims, No Drawings

ANTI-ACNE COMPOSITION

TECHNICAL FIELD

Acne vulgaris and othr types of acne and acneiform skin maladies associated with the hyperplasia of the sebaceous follicle are often treated by the oral administration of antibiotics. Tetracycline has been the traditional drug of choice, but other antibiotics such as erythromycin, lincomycin and clindamycin have also been prescribed for this use. While oral adminstration of these drugs is often effective in treating acne, oral therapy has several disadvantages. For example, the oral administration of antibiotics subjects the entire body to the antibiotic composition; yet, in acne, only the skin is affected. Moreover, almost all antibiotics have some undesirable side effects when taken orally.

In contrast with oral dosing in the treatment of acne, topical application of antibiotics delivers the antibiotic to the afflicted situs and minimizes the antibiotic levels in the circulatory and gastrointestinal systems. Undesirable side effects occurring from oral administration of the drug are greatly reduced, and yet, properly administered in the manner disclosed herein, the therapeutic benefits of topical application are comparable with, or superior to, those derived by oral administration.

A problem with this approach is that the effectiveness of any particular antibiotic as a topical treatment of acneiform skin diseases depends significantly upon the particular skin penetrating vehicle with which it is used.

One agent, isopropyl myristate, has been used with some success in enhancing the percutaneous penetration of erythromycin. However, isopropyl myristate has the undesirable characteristic of promoting the formation of comedones, or blackheads. Thus, it would be desirable to develop new, more dermatologically acceptable penetration enhancers for erythromycin.

Unfortunately, the field of percutaneous absorption remains highly empirical. A leader in this field, Dr. Richard B. Stoughton, has aptly summarized the problem: There are two rather distinct groups of researchers in the field of percutaneous absorption. They are probably best classified as the theoreticians and the practitioners.

The theoreticians are primarily physical chemists who establish strict mathematical relationships of penetration based on general theory and observations of simple membrane structures. In general, they try to avoid working with human or animal skin because these perverse models generally fail to substantiate their predicitons based on simpler systems and theoretical models.

The practitioners have to admit to their studies being more an art than a science but they have the responsibility (and the great advantage) of working with a live, functioning model. Without detailed knowledge of higher mathematics or physical chemistry, these practitioners are best described as belonging to the "apply and observe" school. (Dr. R. B. Stoughton, *J. Invest. Derm.*, 63 (4):305-305 (1974)).

This invention relates to erythromycin-containing compositions which have been empirically determined to cause erythromycin to penetrate skin when applied topically.

BACKGROUND ART

French Pat. No. 2,383,667, S. Desjonqueres, bearing the legend "Date de la mise a la disposition du public de la demande ... B.O.P.I.-"Listes" n. 41 du 13-10-1978" describes topical erythromycin compositions in which rapid penetration of the antibiotic into the sebaceous follicles is achieved. The excipient base include alkyl esters of fatty acids such as lauric, linoleic, myristic and oleic acids.

Compositions for topical treatment of acne are known. Smith, U.S. Pat. No. 3,952,099, issued Apr. 20, 1976, discloses compositions for treating acne lesions by topical application of tetracycline antibiotics in a skin penetration vehicle comprising sucrose monooleate, decyl methyl sulfoxide and alcohol.

Stoughton, U.S. Pat. No. 3,969,516, issued July 13, 1976, and *Arch. Dermatol.*, 84 182 (1976), discloses a method for topically treating acne by applying formulations containing various antibiotics in N-methyl-2-pyrrolidone. The data presented are said to indicate that tetracycline in a pyrrolidone-based penetrating vehicle does not effectively control the inflammatory lesion of acne. In addition to tetracycline, compositions of erythromycin, erythromycin derivatives and clindamycin in the same vehicle were studied. The combination of erythromycin and N-methyl-2-pyrrolidone gave results which were assertedly better than tetracycline in the same vehicle, whereas the antibiotic lincomycin gave superior results in controlling the inflamed lesions.

DISCLOSURE OF THE INVENTION

This invention relates to antibiotic compositions especially adapted for the treatment of skin disorders and dermatoses of bacterial origin, including Acne vulgaris and other acneiform skin diseases (hereafter "acne"). The compositions herein comprise a safe and effective amount of erythromycin and/or compounds of erythromycin and a pharmaceutically acceptable penetrating carrier. A method for treating acne and bacterial dermatoses comprises the topical application of compositions of the foregoing type to the afflicted situs of the skin of a human or lower animal in need of such treatment.

By "afflicted situs" is meant the area of the skin which is inflamed, the acne comedones, papules, pustules, and cysts (acne lesions) and the skin immediately surrounding this area.

By "antibiotic agent" is meant erythromycin base and derivatives of erythromycin. These antibiotic agents can be used alone or in combination in the present compositions.

By "pharmaceutically acceptable" and "dermatologically acceptable" is meant that the ingredients are suitable for use in contact with the skin and tissues of humans and lower animals without any untoward physiological response, commensurate with a reasonable benefit/risk ratio.

By "safe and effective amount" is meant an amount which is effective to alleviate the inflammation and the lesions of the dermatological condition and yet cause no undesirable side effects (at a reasonable benefit/risk ratio). For topical application, a dose range of antibiotic composition of from about 0.1 mg/cm$^2$ pre day to about 25 mg/cm$^2$ per day is effective. The dosage can vary from patient to patient, depending on such factors as the severity of the disease, the frequency of application, the area of the body which is afflicted, and the particular erythromycin compound being applied.

By "topical application" is meant directly spreading or laying on epidermal tissue. The application can be made by rubbing, by using medicated pads, or by any other convenient means By "erythromycin" is meant erythromycin base produced by the strain of *Streptomyces erythreus*. The term includes both erythromycin base and/or its hydrated crystals. By the term "derivatives of erythromycin" is meant the salts between erythromycin base and acids, as well as the ester derivatives of erythromycin. Nonlimiting examples of derivatives of erythromycin include: erythromycin estolate, which is the lauryl sulfate salt of the propionic acid ester of erythromycin; erythromycin glucoheptonate, which is the glucoheptonic acid salt of erythromycin; erythromycin lactobionate, which is prepared from erythromycin base and lactobiono- -lactone; erythromycin stearate, which includes both the stearic acid salt of erythromycin and the stearic acid ester of erythromycin; and erythromycin ethyl succinate, which is the ester of erythromycin and ethyl succinic acid.

The "penetrating carriers" are more fully described hereinafter.

By "penetration-enhancing amount" of the penetrating carriers described herein is meant an amount sufficient to deliver clinically effective amounts of erythromycin or a derivative of erythromycin through intact skin within 18 hours. Penetration enhancing amounts of the penetration enhancers disclosed herein can be determined by the skin penetration testing techniques described hereinafter.

By "skin disorders and dermatoses of bacterial origin" is meant both primary infectious (pyrogenic) processes, and secondary cutaneous manifestations of infection elsewhere in the body. Among the primary pyodermas are included impetigo, such as impetigo contagiosa and impetigo bullosa; deep and superficial folliculitis, including follicular impetigo, sycosis barbae, pyoderma faciale and folliculitis decalvans; furuncles and carbuncles; paronychial infections; ecthyma; erysipelas; cellulitis; lymphangitis; and erythrasma. Typical secondary bacterial infections include those caused by burns, eczematous dermatitis, including exfoliative erythrodermas; chronic ulcers; dermatophytosis; traumatic lesions; and vesicular or bullous eruptions such as varicella and pemphigus. Other distinctive clinical dermatologic entities include secondary folliculitis such as acne conglobata or hidradenitis suppurativa; infectious eczematoid dermatitis; intertrigo; pilonidal and sebaceous cysts; infectious gangrene; and necrotizing ulcers. Unusual cutaneous infections include cutaneous diphtheria; listeriosis; bartonellosis; and animal-born diseases.

A more detailed description of the diagnosis and antibiotic therapy of the foregoing and related diseases can be found in *Dermatology in General Medicine*, Fizpatrick, et al., eds., pages 1679 et seq. (1971), the disclosures of which are fully incorporated herein by reference.

"Lauryl alcohol" is 1-dodecanol. It is insoluble in water and soluble in alcohol and ether.

"Diisopropyl sebacate" is the 2-propyl diester of decanedioic acid. It is slightly soluble in water, and freely soluble in alcohols, esters and ketones.

"Dibutyl sebacate" is the n-butyl diester of decanedioic acid.

"Dioctyl adipate" is employed herein to refer to both the n-octyl and the 2-ethyl-hexyl diesters of hexanedioic acid.

"Propylene glycol dipelargonate" is the n-nonanoic acid diester of 1,2-propanediol.

"Ethyl laurate" is the ethyl ester of n-dodecanoic acid.

"Butyl laurate" is the n-butyl ester of n-dodecanoic acid.

"Ethyl myristate" is the ethyl ester of n-tetradecanoic acid.

"Butyl myristate" is the butyl ester of n-tetradecanoic acid.

"Isopropyl palmitate" is the 2-propyl ester of n-hexadecanoic acid. It is used as an emollient and emulsifier in lotions, creams, and similar cosmetic products. "Isopropyl isostearate" is the coined name for the 2-propyl esters of various isomers, primarily of the methyl-branched series, of $C_{18}$ saturated fatty acids of the formula $C_{17}H_{35}COOH$.

"2-ethyl-hexyl pelargonate" is the 2-ethyl-hexyl ester of n-nonanoic acid.

"Butyl benzoate" is the butyl ester of benzoic acid. Similarly, "benzyl benzoate" is the benzyl ester of benzoic acid, and "benzyl salicylate" is the benzyl ester of orthohydroxybenzoic acid. "Dibutyl phthalate" is the butyl diester of ortho-benzenedicarboxylic acid.

"Oleyl alcohol" is cis-9-octadecen-1-ol. It is the unsaturated alcohol derived from oleic acid.

"Diethyl sebacate" is the ethyl diester of decanedioic acid.

"Dioctyl sebacate" is the 2-ethyl-hexyl diester of decanedioic acid.

"Dioctyl azelate" is the 2-ethyl-hexyl diester of nonanedioic acid.

"Hexyl laurate" is the hexyl ester of dodecanoic acid.

"Ethyl caprate" is the ethyl ester of decanoic acid.

"Butyl stearate" is the butyl ester of octadecanoic acid.

All of the foregoing are known compounds; all are articles of commerce, available commercially from a variety of sources in laboratory and/or industrial quantities.

By "comprising" is meant that various other compatible ingredients may be present in the compositions in such a proportion as will not adversely affect the stability and penetrating effectiveness of the basic composition. The term "comprising" thus encompasses and includes the more restrictive terms "consisting" and "consisting essentially of" within its scope.

All percentages are by weight, unless otherwise specified herein.

BEST MODE

The compositions of the present invention comprise (1) a minor proportion of an antibiotic agent selected from the group consisting of erythromycin and derivatives of erythromycin; and (2) a major proportion of pharmaceutically-acceptable penetrating carrier, comprising: (a) a penetration-enhancing amount of a penetration enhancer which comprises a member selected from the group consisting of lauryl alcohol, diisopropyl sebacate, oleyl alcohol, diethyl sebacate, dioctyl sebacate, dioctyl azelate, hexyl laurate, ethyl caprate, butyl stearate, dibutyl sebacate, dioctyl adipate, propylene glycol dipelargonate, ethyl laurate, butyl laurate, ethyl myristate, butyl myristate, isopropyl palmitate, isopropyl isostearate, 2-ethyl-hexyl pelargonate, butyl benzoate, benzyl benzoate, benzyl salicylate, and dibutyl phthalate, and mixtures thereof; and (b) the balance comprising a dermatologically acceptable alcohol.

In general, the penetration enhancers are effective in concentrations of from about 20% to about 80%, and above. Preferably, the compositions will contain sufficient penetration enhancer to promote penetration of the erythromycin, and sufficient dematologically acceptable alcohol to provide a conveniently usable and esthetically acceptable liquid, lotion, gel, or the like. Thus, the compositions of the present invention preferably contain from about 30% to about 60% of the penetration enhancer, most preferably about 30%, and from about 40% to about 70% of the alcohol.

Of course, optional ingredients may be added, including pigments and perfumes to provide cosmetic acceptability, emollients, humectants, and natural oils to provide skin conditioning benefits, and thickening, gelling, and film forming agents such as carboxymethyl cellulose, polyethylene glycols, carbomers, and "Carbosets TM."Preservatives, such as the "parabens" (methyl, ethyl, propyl and butyl esters of parahydroxybenzoic acid), and benzyl alcohol can be used to provide protection against contamination by fungi and non-susceptible bacteria.

The foregoing compositions preferably comprise from about 0.1% to about 10% of the antibiotic agent, more preferably from about 2% to about 5% erythromycin. Most preferable, from the standpoint of efficacy, stability, and safety, is a concentration of erythromycin or erythromycin derivative which provides about 4% erythromycin base equivalent.

Preferred antibiotic agents are erythromycin base and organic ester derivatives of erythromycin, especially erythromycin ethyl succinate. Also preferred are erythromycin derivatives selected from the group consisting of erythromycin propionate, erythromycin estolate, and erythromycin stearate. Selection of an antibiotic agent from among erythromycin and derivatives of erythromycin will depend in many cases on the solubility of erythromycin or the erythromycin derivatives in the particular penetrating vehicle being used. In some cases, limited solubility of the antibiotic agent in the vehicle selected will determine the maximum concentration of antibiotic that can be used.

Among the penetrating carrier materials, diisopropyl sebacate is especially preferred because of its known safety and compatibility in compositions for topical application to skin. An especially preferred composition containing diisopropyl sebacate comprises (1) about 4% erythromycin; (2) about 30% diisopropyl sebacate; and (3) about 66% ethanol.

Dermatologically acceptable alcohols can be selected from the simple short-chain alcohols and the toxicologically safe polyols. Examples include ethanol, isopropanol, propylene glycol, and glycerol. Especially prefered is a member selected from the group consisting of ethanol, isopropanol, and mixtures thereof. While the examples herein employ absolute ethanol, it is to be understood that both absolute (100%) and 95% ethanol are acceptable for the practice of this invention. Denatured ethanol can be used so long as the denaturant is toxicologically acceptable and does not affect the stability of the antibiotic or its efficacy, or the penetrating characteristics of the vehicle.

Water can be present in the compositions of this invention without deleteriously affecting the penetration of the antibiotic agent. However, the presence of substantial amounts of water causes erythromycin and erythromycin derivatives to become unstable on prolonged storage. Thus, the preferred compositions of this invention are substantially water-free or contain less than about 5% water. In light of this, the preferred compositions which contain ethanol as a dermatologically acceptable alcohol will employ absolute ethanol.

Use

When the compositions of the present invention are used in the treatment of skin disorders and dermatoses of bacterial origin, the amount of composition topically applied and treatment regimen will vary, depending upon the particular disease being treated and the susceptibility of the causative organisms to erythromycin antibiotics, the patient, the severity of the disease state, and like factors which must be considered by the attending physician.

When the compositions of this invention are used in the topical treatment of acne, the preferred treatment will comprise applying a safe and effective amount of the composition to the afflicted situs on the skin. An effective dosage is about 0.1 mg/cm$^2$ to about 25 mg/cm$^2$ of the antibiotic composition per day. It is preferred to cleanse the skin prior to treatment, and any soap or detergent composition suitable for washing the skin can be employed. The treatment is more effective if topical applications are made 2 to 4 times per day.

INDUSTRIAL APPLICABILITY

The problems encountered in the topical administration of antibiotics have been the stability of the drug in the carrier or vehicle and the development of a carrier vehicle allows the drug to penetrate the skin, thus facilitating the delivery of the antibiotic. The selection of the appropriate carrier for an antibiotic agent is critical. Not all delivery systems and penetrating aids will facilitate the diffusion of a given antibiotic agent through the skin barrier. The penetrating carrier must be compatible with the antibiotic; it must be non toxic; and the formulation must be stable.

Skin Penetration Testing

In order to determine the best penetrating carriers for erythromycin and derivatives of erythromycin, a diffusion study was carried out using the skin of hairless mice. Briefly, the study employed mouse skin which was placed in a vertical position between a lower, capped, diffusion cell and an upper, open cell. A normal saline solution was added to the lower diffusion cell, abutting the subcutaneous side of the mouse skin, and the test composition comprising a solution of the antibiotic agent and the penetrating carrier was added to the diffusion cell abutting the epidermal side of the mouse skin. A small glass bead was added to the lower diffusion cell to provide mixing.

This cell assembly was kept in a constant-temperature room at about 31° C. The diffusion time used for the test was about 18 hours.

At the end of this time period, each diffusion cell assembly was opened and the diffusate from the cell abutting the subcutaneous side of the skin was filtered by expressing the liquid through a disposal filter attached to a plastic disposable syringe. This diffusate was then submitted for microbiological agar diffusion assay done in accordance with the procedure described at 21 C.F.R. 436.105. This test provides a measure of the passage of active erythromycin antibiotic through the skin.

Table 1 lists a representative number of penetrating carriers and other tested materials and their activity, as micrograms erythromycin which penetrated through the mouse skin, per milliliter (mcg/ml) of diffusate.

TABLE 1

| Test Material | Hrs. | Penetration-mcg./ml. |
|---|---|---|
| Propylene glycol dipelargonate | 18 | 248 |
| Polyoxypropylene 15 stearyl ether | 18 | 95* |
| Standamul HE TM (Polyol fatty acid ester) | 18 | 0* |
| Propylene glycol | 18 | 0* |
| Benzyl alcohol | 18 | 0* |
| Carbowax TM 400 | 18 | 0* |
| Octyl alcohol | 18 | 132* |
| 1,2-Butanediol | 18 | 0* |
| 2,3-Butanediol | 18 | 0* |
| 1,3-Butanediol | 18 | 0* |
| POE ester of oleyl alcohol | 18 | 121* |
| Phenethyl alcohol | 18 | 0* |
| Oleyl alcohol | 18 | 197 |
| Cyclohexanol | 18 | 0* |
| 2-Phenoxyethanol | 18 | 0* |
| Lauryl alcohol | 18 | 254 |
| Dioctyl adipate | 18 | 234 |
| Diethyl adipate | 18 | 0* |
| Dicapryl adipate | 18 | 235 |
| Diisopropyl adipate | 18 | 103* |
| Diisopropyl sebacate | 18 | 268 |
| Dibutyl sebacate | 18 | 207 |
| Diethyl sebacate | 18 | 158 |
| Dimethyl sebacate | 18 | 91* |
| Dioctyl sebacate | 18 | 181 |
| Dibenzyl sebacate | 18 | 132* |
| Diethyl suberate | 18 | 0* |
| Dibutyl suberate | 18 | 36* |
| Dioctyl azelate | 18 | 180 |
| Dibutyl azelate | 18 | 86* |
| Dimethyl azelate | 18 | 64* |
| Dibutyl succinate | 18 | 73* |
| Diethyl succinate | 18 | 0* |
| Dibutyl phthalate | 18 | 227 |
| Dimethyl phthalate | 18 | 0* |
| Didecyl phthalate | 18 | 55* |
| Ethyl myristate | 18 | 296 |
| Butyl myristate | 18 | 243 |
| Isopropyl palmitate | 18 | 285 |
| Ethyl laurate | 18 | 243 |
| Decyl oleate | 18 | 126* |
| 2-ethyl-hexyl pelargonate | 18 | 228 |
| Isopropyl isostearate | 18 | 204 |
| Butyl laurate | 18 | 214 |
| Benzyl benzoate | 18 | 230 |
| Butyl benzoate | 7 | 177 |
| Ethyl benzoate | 18 | 0* |
| Benzyl 2-acetoxy benzoate | 18 | 0* |
| Hexyl laurate | 18 | 201 |
| Ethyl caprate | 18 | 236 |
| Ethyl caprylate | 18 | 162 |
| Ethyl caproate | 18 | 66* |
| Butyl stearate | 18 | 198 |
| Benzyl salicylate | 18 | 236 |
| Ethyl salicylate | 18 | 131* |
| 20% Benzyl benzoate + 20% Ethyl laurate | 18 | 253 |
| 10% Benzyl salicylate + 40% Ethyl laurate | 18 | 269 |
| 40% Dibutyl sebacate + 10% Benzyl salicylate | 18 | 241 |

*Does not represent acceptable delivery
0* indicates that no readable zone was produced at the dilution tested.

In addition, the following materials were tested in the foregoing manner and were not found to deliver clinically effective concentrations of erythromycin.

Squalane
Castor oil
N-methyl-2-pyrrolidone
Ethyl lactate
2,4-pentanedione
Silicone 344
Cyclohexanone
Salicylic acid + isopropyl myristate
Salicylic acid + propylene glycol
Salicylic acid + dibutyl sebacate
Salicylic acid + propylene glycol dipelargonate
Solketal TM + Propylene glycol dipelargonate
Propylene glycol dipelargonate + lactic acid
Propylene glycol dipelargonate + ethyl lactate
Dimethyl sulfoxide
Propylene glycol + monoolein The following Examples illustrate the practice of this invention, without intending to be limiting thereof.

EXAMPLE I

| Ingredient | Weight % |
|---|---|
| Erythromycin base | 4% |
| Ethanol | 66% |
| Diisopropyl sebacate | 30% |

The above ingredients are blended mechanically to provide a fluid composition suitable for topical application to skin. In the composition of Example I, the diisopropyl sebacate markedly enhances the skin penetration of the erythromycin.

The composition of Example I is especially useful in the treatment of common acne (acne vulgaris) and similar acneiform bacterial dermatological conditions.

A person afflicted with acne lesions is treated by topically applying the composition of Example I to the afflicted areas of skin (typically the face, neck and shoulders) at a rate of 3 mg./cm$^2$ of antibiotic composition twice a day for 6 weeks. At the end of this period, there is a substantial reduction in the number of acne lesions, and the inflammation is reduced.

Erythromycin ethylsuccinate can be substituted for the erythromycin base, in an amount which provides 4% erythromycin base equivalent, with equivalent results.

EXAMPLE II

| Ingredient | Weight % |
|---|---|
| Erythromycin lactobionate | 10% |
| Isopropyl alcohol | 40% |
| Ethyl laurate | 50% |

The above ingredients are blended mechanically to provide a fluid composition suitable for topical application to skin. In the composition of Example II, the ethyl laurate markedly enhances the skin penetration of the erythromycin.

This composition is especially useful in the treatment of impetigo and similar dermatologic disorders caused by Staph. aureus and/or group A Streptococci, when applied topically at a rate of from about 0.1 mg/cm$^2$ to about 25 mg./cm$^2$ per day.

Erythromycin propionate can be substituted for the erythromycin lactobionate, in an amount which provides 10% erythromycin lactobionate equivalent, with equivalent results.

Oleyl alcohol, dibutyl sebacate, or dioctyl sebacate can be substituted for the ethyl laurate in the composition of Example II, with equivalent results.

EXAMPLE III

| Ingredient | Weight % |
|---|---|
| Erythromycin estolate | 0.5% |
| Ethanol | 15% |
| Isopropyl Alcohol | 24.5% |

EXAMPLE III-continued

| Ingredient | Weight % |
| --- | --- |
| Dioctyl Adipate | 60% |

The above ingredients are blended mechanically to provide a fluid composition suitable for topical application to skin. In the composition of Example III, the dioctyl adipate markedly enhances the skin penetration of the erythromycin.

This composition is especially useful in the treatment of folliculitis, including follicular impetigo, sycosis, barbae, pyoderma faciale, and folliculitis decalvans. The treatment regimen described in Example I is especially suitable.

When used topically in the manner disclosed herein, the topical use of erythromycin estolate offers marked advantages over the systemic administration of the same compound, in that the erythromcin estolate exerts its antibiotic action primarily at the site of topical application, with minimal systemic exposure to the drug. In so doing, the hepatotoxicity sometimes noted with systemic administration of erythromycin estolate is avoided.

Erythromycin stearate can be substituted for the erythromycin estolate, in an amount which provides equivalent to 0.5% erythromycin estolate, with equivalent results.

Dioctyl azelate, hexyl laurate, and ethyl caprate can be substituted for the dioctyl adepate of the composition of Example III, with equivalent results.

EXAMPLE IV

| Ingredient | Weight % |
| --- | --- |
| Erythromycin glucoheptonate | 0.1% |
| Ethanol | 40% |
| Ethyl cellulose | 10% |
| Dibutyl sebacate | Balance |

This composition provides a creamy gel base adapted to topical application to skin via, for example, a roll-on bottle. The penetrating vehicle for the erythromycin glucoheptonate makes this composition especially suitable for the treatment of deep bacterial skin disorders such as furuncles and carbuncles.

Erythromycin laurate 0.1% can be substituted for the erythromycin glucoheptonate, with equal effect.

The composition of Example IV can be applied topically to cattle, sheep, horses and other domestic animals in the treatment of infected insect bites, mange, and other skin diseases and dermatoses of bacterial origin.

EXAMPLE V

| Ingredient | Weight % |
| --- | --- |
| Erythromycin, hydrated crystals | 5% |
| Carbopol TM 940 | 0.1% |
| Triethanolamine | 0.5% |
| Propylene glycol dipelargonate | 25% |
| Flesh-tone pigment | q.s |
| Ethanol | bal. |

The composition is mechanically blended at low shear (to avoid excessive entrainment of air), with the triethanolamine added last, forming a gel suitable for use in the treatment of eczematous dermatitis, dermatophytosis, and ecthyma, and most common bacterial skin disorders.

Lauryl alcohol can be substituted for the propylene glycol dipelargonate, with equivalent enhancement of erythromycin penetration.

EXAMPLE VI

| Ingredient | Weight % |
| --- | --- |
| Erythromycin base | 5% |
| Isopropyl alcohol | 50% |
| Propylene glycol dipelargonate | 20% |
| Butyl laurate | 25% |

The composition of Example VI is formulated as a fluid composition suitable for topical administration by simple mechanical mixing of the components.

Other blends of penetration enhancers which can be used in lieu of the propylene glycol dipelargonate-butyl laurate vehicle include 3:1 isopropyl palmitate and isopropyl isostearate, 1:1 butyl and ethyl myristate; 2:1 butyl laurate and butyl stearate; and 1:2 benzyl benzoate and benzyl salicylate. In each instance, equivalent results are obtained.

EXAMPLE VII

| Ingredient | Weight % |
| --- | --- |
| Erythromycin estolate | 2% |
| 2-ethyl-hexyl pelargonate | 30% |
| Flesh-tone pigment | q.s. |
| Perfume | q.s. |
| Carboset 514 TM | 0.25% |
| NaOH | q.s. |
| Isopropyl alcohol | Bal. |

The formulation of Example VII is prepared by mixing the ingredients at low shear, to avoid excessive air entrainment, with the sodium hydroxide added last.

The composition of Example VII, with the appropriate pigment and perfume, provides a highly effective medicated makeup base for use in the treatment of acne.

In the composition of Example VII, butyl benzoate provides equivalent results when substituted for the 2-ethylhexyl pelargonate.

What is claimed is:

1. A composition for topical application to skin in the treatment of skin disorders and dermatoses of bacterial origin, comprising:
    (1) a minor proportion of an antibiotic agent selected from the group consisting of erythromycin and derivatives of erythromycin; and
    (2) a pharmaceutically-acceptable penetrating carrier comprising
        (a) a penetration enhancing amount of diisopropyl sebacate; and
        (b) the balance comprising a dermatologically acceptable alcohol, or mixture thereof.

2. A composition according to claim 1 wherein the dermatologically acceptable alcohol is a member selected from the group consisting of ethanol, isopropanol, and mixtures thereof.

3. A composition according to claim 1 which comprises from about 0.1% to about 10% of the antibiotic agent.

4. A composition according to claim 2 wherein the antibiotic agent is erythromycin.

5. A composition according to claim 3 which comprises from about 2% to about 5% erythromycin.

6. A composition according to claim 2 wherein the antibiotic agent is an organic ester derivative of erythromycin.

7. A composition according to claim 6 wherein the organic ester derivative of erythromycin is erythromycin ethyl succinate.

8. A composition according to claim 3 wherein the derivative of erythromycin is selected from the group consisting of erythromycin propionate, erythromycin estolate, and erythromycin stearate.

9. A composition according to claim 5, comprising:
   (1) about 4% erythromycin;
   (2) about 30% diisopropyl sebacate; and
   (3) about 66% ethanol.

10. A method of topically treating skin disorders and dermatoses of bacterial origin in humans and lower animals in need of such treatment, comprising applying topically to the afflicted situs a safe and effective amount of a composition according to claim 1.

11. A method of treating acne by applying topically to the afflicted situs from about 0.1 mg./cm.$^2$ to about 25 mg./cm.$^2$ of a composition according to claim 1.

12. A method according to claim 10 or 11 in which the antibiotic agent is erythromycin.

13. A method according to claim 10 or 11 in which the antibiotic agent is erythromycin ethylsuccinate.

14. A method according to claim 13 in which the composition comprises:
   (1) about 4% erythromycin;
   (2) about 30% diisopropyl sebacate; and
   (3) about 66% ethanol.

* * * * *